United States Patent [19]  [11] 4,171,352
Wolgemuth et al.  [45] Oct. 16, 1979

[54] QUANTITATIVE EVALUATION OF ENTERIC MICROBIAL OVERGROWTH

[75] Inventors: Richard L. Wolgemuth, Hatfield, Pa.; Kenneth M. Hanson; Peter H. Zassenhaus, both of Columbus, Ohio

[73] Assignee: Polysciences, Inc., Warrington, Pa.

[21] Appl. No.: 826,539

[22] Filed: Aug. 22, 1977

[51] Int. Cl.$^2$ .................... A61K 29/00; G01N 33/16
[52] U.S. Cl. .................................................. 424/9
[58] Field of Search .................. 424/230, 9, 310, 315, 424/317

[56] References Cited

U.S. PATENT DOCUMENTS 3,745,212  7/1973  de Benneville ........................ 424/9

OTHER PUBLICATIONS

Lack et al, J. of Lipid Res., vol. 14, 1973 pp. 367-370.
Hill et al, Gut., vol. 9, 1968 pp. 22-27.
Wolgemuth, et al, Am. J. Dig. Dis., vol. 21, No. 9, Sep. 1976 pp. 821-826.
Wolgemuth et al Chem. Abs., vol. 85, 1976 Abs. No. 173791s.

*Primary Examiner*—Anna P. Fagelson
*Attorney, Agent, or Firm*—Raymond Underwood

[57] ABSTRACT

A quantitative evaluation of the intestinal microflora is made by administering to an animal organism an effective amount of novel chemical conjugates of a bile acid or related acid with an amino acid which will be cleaved from the bile or related acid by the enzymes elaborated by the intestinal microflora and then measuring the amount of the released amino acid in the urine after a predetermined time interval. The novel compounds and their use in in vitro tests are included in the invention.

4 Claims, No Drawings

QUANTITATIVE EVALUATION OF ENTERIC MICROBIAL OVERGROWTH

This invention relates to in vivo testing or to diagnostic procedures on animal organisms including humans and particularly to a method for the assay of gastrointestinal microbial overgrowth. Also, the invention includes novel compounds or chemical conjugates which are useful in carrying out these tests or procedures.

A proliferation in the upper intestine of the microorganisms, which are normally there in small amounts, may cause a variety of malfunctions or feelings of malaise. This bacterial overgrowth may be caused by several conditions such as the prolonged oral administration of antibiotics and other bactericidal agents. The antibiotic may be selective in its germicidal action and it consequently may upset the natural competitive balance of the microorganisms in the upper intestine. This may result in an excessive growth of a resistant organism.

Such an overgrowth of an intestinal bacterium can cause on or more illness symptons such as steatorrhea, diarrhea, intestinal epithelial disruption by microbial products and other intestinal dysfunctions. The patient can experience a condition which ranges from a moderate feeling of discomfort to an overall severe sickness. Unfortunately, these adverse symptoms are caused by conditions other than an intestinal microbial overgrowth and a physician often is faced with the problem of determining what the actual causative factor may be.

In humans, for instance, if a person has diarrhea, the doctor may not know whether it is caused by an intestinal microbial overgrowth or whether it is caused by a serious pancreatic or hepatic malfunction. He can narrow down the nature of the disorder by using a variety of available diagnostic procedures but most of them are difficult and expensive to perform. Surgical exploration is especially undesirable and consequently a test which is easy to perform and which will establish or eliminate intestinal bacterial overgrowth would be most welcome. This same problem of determining which one of several possible physical disorders accounts for the particular sickness symptom, arises as well with animals.

There are now available several in vivo tests for evaluating intestinal microbial overgrowth. Some of these known tests are disclosed in a journal article which we co-authored having the title "A New Substrate for the Rapid Evaluation of Enteric Microbial Overgrowth". This article is hereby incorporated into this disclosure by this reference. It appears in *American Journal of Digestive Diseases*, New Series, Vol. 21, No. 9 (September 1976), pages 821-826. As the journal article points out, the known assay tests require the use of expensive $^{14}$C-labeled glycocholate or the complications of intubation or an analysis of intestinal aspirates. Moreover, the past tests have not been standardized.

The assay method of the present invention overcomes the disadvantages of the tests used in the past as inexpensive diagnostic material is used, the procedure is a simple one and the results are reliable. This test makes use of the known fact that the microflora which are normally present in the intestine produce an enzyme which deconjugates bile salts. One of the normal ingredients of bile fluids is the conjugate of cholic acid known as glycocholic acid and the enzymes of the normal intestinal bacteria deconjugate it by hydrolysis so that cholic acid and glycine separately appear. If the amount of glycocholic acid which is produced by the bile were fixed or determinable it might be possible to run an analysis for the glycine which is released by the bacterial enzyme and thereby make a quantative determination of the intestinal bacteria which produced the deconjugation.

This is because there appears to be a nearly straight line relationship between the extent of hydrolysis of a bile acid conjugate and the quantity of intestinal bacteria which are present. That is, an increase in the colony size of the bacteria will produce an increased deconjugation of glycocholic acid as measured by the amount of released glycine.

The invention is practiced by internally, preferably orally, administering to the organism a measured, effective amount of a synthetic conjugate of a selected bile acid or its chemical derivatives and an amino acid, the conjugate linkage being one which will be cleaved by hydrolysis by the enzymes which are released by the microorganisms. The amino acid must be chosen from those which are pharmacologically acceptable to the body, will be absorbed in the body, be excreted in the urine and be detectable quantatively in the urine. Representative of such useable conjugates is that of para-aminobenzoic acid (PABA) and cholic acid. They form an amide or peptide linkage which is broken by hydrolysis by the intestinal bacterial enzymes so that PABA is released in the intestine, absorbed in the blood stream and is subsequently excreted in the urine. The amount of PABA which is found in the urine is compared to that which is known to be excreted in the same time by a normal asymptomatic identical organism that has been given that same amount of the same PABA-cholic acid conjugate.

This test, if a large amount of PABA is found in the urine, can be taken as an indication that there is an abnormally large proliferation of intestinal bacteria and it suggests to a physician or veterinarian that remedial steps be taken to reduce the overgrowth. On the other hand, if there is a normal amount of PABA in the urine, it can be taken as a quite reliable indication that the illness is not due to an intestinal bacterial overgrowth and it suggests to the physician or veterinarian that he look for other causative factors. The feature of the invention, therefore is that it provides the doctor with an inexpensive and easily and readily performed test that enables him to rule out intestinal bacterial overgrowth as the cause of the patient's distress. Moreover, the test is non-toxic, non-surgical and relatively convenient to the patient.

It has been mentioned above that a representative conjugate is PABA-cholic acid and the invention will be further described now with reference to its synthesis and use but it is to be understood, as will be explained, that other bile acids and their chemical derivatives may be used instead of cholic acid. Cholic acid is preferred because it is non-toxic and as a natural product is quite acceptable in the body; additionally, it is relatively inexpensive as it is extracted from beef and other animal bile. PABA is the preferred amino acid but other physiologically acceptable amino acids may be used as the analyzable component as will be explained. As is mentioned above, the chosen amino acid, like PABA, must be deconjugated from the peptide and be absorbed in the body as it is released from the conjugate and must be eliminated in the urine so that it can be quantatively evaluated.

Synthesis of PABA conjugate of cholic acid.

To form the amide or peptide linkage between the carboxyl group of cholic acid or its derivative and the amino group of the analyzable entity, it is convenient to use a known chemical reaction and subsequent isolation and purification of the conjugate. A representative procedure if that described in, J. Lipid Research, 14, 367-370, (1973) by Lack, Dorrity, Walker and Singletary. Utilizing its process the PABA-cholic acid conjugate used in our tests was made by the following procedure.

Cholic acid (100 g, 0.24 mole) was dissolved in 2 liter of ethyl acetate and 2 liter of acetone. The solution was heated to 50° and ethyl p-aminobenzoate (53 g, 0.26 mole) was added. The solution was then adjusted to pH 8 by the addition of 30 ml of triethyl amine and EEDQ (90 g, 0.36 mole) was added. The solution was stirred and heated at 50° C. for 50 hours. The solution was then concentrated to 200 ml on a rotary evaporator using a water bath at 50°. The concentrated solution was diluted to 1 liter with 0.1 N sodium hydroxide and the aqueous phase extracted 3 times with 500 ml of ethyl acetate. The organic layer was then washed successively with 3×200 ml of 1 N hydrochloric acid, 1×200 ml of water, 3×200 ml 1% sodium bicarbonate, and 2×200 ml water and then was evaporated under vacuum to a thick brown oil. The residual oil was diluted with 500 ml of methanol and 1500 ml of 1 N sodium hydroxide, and stirred for two days at ambient temperature. The volume of solution was then reduced to 100 ml and extracted with 3×200 ml ethyl acetate followed by 200 ml ether. The remaining aqueous layer was acidified to pH 1 with concentrated hydrochloric acid and the oily precipitate was left to crystalize overnight at 5° C.

The precipitate was collected and washed 3 times with 100 ml 1 N hydrochloric acid and 3 times with 100 ml ether. The precipitate was dissolved in 500 ml of ethanol and adjusted to pH 8 by the addition of 200 ml of 1 N sodium hydroxide. The solution was diluted to 100 ml by the addition of ether and left for 18 hours at 5° C. The resulting precipitation was collected, washed with ether, and dried under vacuum to yield 46 g of crude sodium salt, (35% yield). The crude sodium salt, 10 grams, was dissolved in 200 ml of water which was adjusted to pH 1 by the addition of 10 ml of concentrated hydrochloric acid. The resulting precipitate was collected, washed with 100 ml of 1 N hydrochloric acid, followed by 100 ml of ether. The crude acid was dissolved in 100 ml acetone, filtered and the filtrate brought to 500 ml with ether. The solution was then concentrated to 100 ml under vacuum and the resulting white precipitate was collected, washed with ether and dried under vacuum to give 3.3 g of PABA-Cholic acid, mp. 264-268° dec., infra-red exhibited amide absorption at 1690 and 1680 cm-1.

Purity of the compound was assayed by means of thin-layer chromatography (silica gel G-25, 0.25 mm thick, fluorescent 254 plates) using as a solvent benzene-carbon tetrachloride-dioxane-pentyl acetate-isopropanol-glacial acetic acid (10:20:30:40:10:5). PABA, benzocaine, and their conjugates with cholic acid appeared as discrete spots under short-wave ultraviolet light. Cholic acid and the PABA or benzocaine cholic acid conjugates were further indentified by spraying with 5% Phosphomolydate in ethanol and developing at 100° C. for 10 min. The $R_f$s for the reactants and major products were: benzocaine, 0.75; PABA, 0.68; benzocaine-cholic acid conjugate, 0.53; cholic acid, 0.45; and PABA-cholic acid conjugate, 0.40. The Bratton-Marshall test for free aromatic amines revealed less than 1% contamination of the product with free PABA or benzocaine.

Use of PABA-cholic acid conjugate to determine intestinal bacterial overgrowth.

Based on the animal tests which are hereinafter described, 0.5 grams of the conjugate would be orally administered to a person having symptoms which would indicate a possible bacterial overgrowth in the intestines. If the person does not have such an overgrowth, only about 0.02 grams of PABA would appear in the urine collected in the next six hours. This is because a normal occurrence of bacteria in the intestine means that there is only a normal presence of the enzymes which will cleave off the PABA entity of the conjugate so that it will be absorbed in the body and be excreted in the urine. The PABA-cholic acid conjugate which is not deconjugated remains in the body and does not appear in the urine.

However, if the person undergoing the test, excretes, in a six hour period a total of 0.04 grams or more of PABA, this is a strong indication of intestinal bacterial growth. It means that there is such a proliferation of bacterial enzymes in the intestines that considerably more than a normal amount of the PABA-cholic acid conjugate has been deconjugated to yield the PABA.

These relative amounts are based on animal tests and extensive veterinary and clinical tests may show that from 0.5 mg to 2.0 gms. per Kg. body weight, of the conjugate should be orally administered to persons. This would apply to animals as well, such as dogs, cats, horses, etc. Also such tests will establish a more normal PABA excretion amount for organisms not having an overgrowth and this figure will be used as a basis for comparison of the PABA exretion amount in the same organism suspected of having an intestinal bacterial overgrowth. Also, such tests may show that a shorter or a larger period of time is sufficient or required.

Animal tests with PABA-cholic acid conjugate.

Forty male Sprague-Dawley rats (200-300 g) were used in these studies. For experimental purposes the animals were prepared as three different types: normal controls; antibiotic treated, which received a massive oral broadspectrum antibiotic regimen; and bacterial overgrowth, in which the upper small intestine was radically contaminated with fecal material by surgical manipulation. Also the PABA-cholic was administered by means of an oral dosing needle.

Animals to be tested were fasted overnight. The PABA-conjugated bile acid was administered orally in a slightly basic (pH 7.4) aqueous solution. After dosing, the animals were confined individually to stainless-steel metabolism cages. Urine collections were made at 2, 6, 9, 12 and 24 hr after dosing. PABA determination in the urine was made by measuring the total aromatic amine concentration using the Bratton and Marshall procedure.

Oral administration of the compound to normal rats resulted in excretion of the PABA entity; however, due to the absence of microbes in the proximal small bowel, significant amounts of PABA did not appear in the urine until the 12-hr collection period. Colonic bacterial digestion of the conjugate is indicated by the recovery of the PABA entity at this delayed time interval.

In the antibiotic treated group it apparently was not hydrolyzed at any time during its passage through the gastrointestinal tract. The negligible recovery of the PABA tracer presumably was a consequence of the paucity of enteric bacteria and bacterial enzymes in the antibiotic-treated groups.

A markedly different pattern emerged when PABA-cholic was given to rats with a bacterial overgrowth. Oral administration of the substrate to the surgically manipulated rats resulted in a 250% greater excretion of the PABA tracer when compared to the normals at the 6-hr collection. This is explained by the associated large amount of bacterial enzymes elaborated in the intestines by the overgrowth of bacteria.

As is stated above, these animal tests show that the measurement of the PABA excreted in the urine in a set time period after the oral administration of a PABA-cholic acid conjugate is a reliable direct indication of the quantative presence in the intestines of bacteria. If an abnormally large colony of the bacteria exists, there will be a correspondingly large amount of the enzymes which they produce and which cleave PABA-cholic acid conjugate into its PABA entity and its cholic acid entity.

A comparison of the actual PABA eliminated in the urine with the normal amount which would be excreted in the same collection period following an equal oral administration, informs a doctor that there probably is or is not a bacterial overgrowth.

The above discussion is based on the use of a PABA-cholic acid conjugate but as is stated above other cholic acid related acids may be used in place of cholic acid. Representative ones are the following:

desoxycholic acid
chenodesoxycholic acid
lithocholic acid
dehydrocholic acid
cholanic acid
allocholanic acid
dehydrodesoxycholic acid
desoxybilianic acid
isodesoxybilianic acid
bilianic acid
etiocholanic acid
12-ketocholanic acid
hyodesoxycholic acid
norcholanic acid
ursocholanic acid
hyobeoxycholic acid
5-β-cholanic acid-3α,6α-diolacetate
5-β-cholanic acid-3α,12α-diol difurmate
5-β-cholanic acid 7α,12α-diol
5-β-cholanic acid-3α,7α-diol-12-one
7-ketodeoxy cholic acid
7,12-diketocholanic acid
3,12-diketocholanic acid
3,7-diketocholanic acid In place of PABA as the analyzable component of the conjugate, other aromatic amino acids may preferably be used but aliphatic amino acids preferably with 1 to 8 carbon atoms may be used, having in mind that to assay the latter in the urine it will be necessary to use known secondary analysis methods to obtain a quantative figure. Usable aromatic amino acids which may be used are represented by the formula:

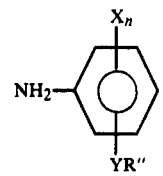

in which R" is a hydroxyl group, a ($C_1$-$C_4$) alkoxy group, a ($C_1$-$C_4$) alkoxyalkoxy group, a ($C_1$-$C_8$) aminoalkylamino group, a ($C_1$-$C_4$) dialkylamino group, a group of the formula —NHCH$_2$COR", or a salt, such as the sodium, potassium, or ammonium salt, of the group in which R" is a hydroxyl group:

Y is a group of the formula —CO— or —SO$_2$—;
X is a hydroxyl group, a ($C_1$-$C_4$)alkyl group, a halogen atom, a ($C_1$-$C_4$)alkoxy group, or a similar substituent which will not interfere with the test efficacy of the conjugate; and n is 0, 1, or 2.

The desired end conjugate is made by selecting the appropriate cholic acid or its derivative from the above list and selecting an amino acid within the above definition and then carrying out the necessary reaction and isolation procedures. In most instances the steps outlined above for making the PABA-cholic acid conjugate will give the wanted adduct but other known processes may be found to be more appropriate. The resulting end conjugate would be administered as above within the range outlined and the urine would be collected and evaluated as explained above.

As is stated above, these new conjugates are a feature of this invention and they may be represented by the formula: Q-Q" in which:

Q is a residue of cholic acid or one of its derivatives as contained in the above list:
Q" is a residue of an aliphatic amino acid as defined above, or it is a residue of an acid represented by the above formula:

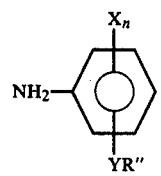

in which the radicals X, Y, R" and n are stated above.

In many instances, for ease of administration, a measured amount of the conjugate can be put into hard gelatin capsules so that each one contains a unit dosage and one or more of them would be administered to add up to the desired total dose to carry out the test. The size of the capsule and the amount in each would of course depend on the size or weight of the person or animal and the complications, if any, of administration.

The conjugate may be put up in the other common pharmaceutical forms using the conventional pharmaceutical excipients and practices. These other forms may be tablets, boluses, packaged powders, aqueous suspensions or solutions, and elixirs with alcohol or other liquids, for example. Care should be taken that no incompatible ingredients are added to the conjugate.

The above description explains and exemplifies the in vivo utility of the invention but the invention also includes the in vitro use of the novel compounds to quantitatively determine the concentration of bacteria in biological fluids. This is based on the showing in our journal article that incubation of the conjugate substrate in vitro with Clostridium welchi powder showed that the bacteria containing cholyl hydrolases do indeed hydrolyze the PABA-conjugates.

An example of an in vitro test contemplated by this invention is the following. Intestinal fluids are aspirated from the duodemun and other sites in the small intestine. The intestinal fluid (2–10 ml) is added to an equal volume of phosphate buffer at pH 5.8. One ml of a PABA-cholic solution is added to this mixture and incubated in a water bath at 37° C. At selected time intervals between 0 and 60 minutes, 1 ml aliquots are removed and added to 4 ml 10% TCA. The solution is centrifuged and the free PABA concentration in the supernatant determined by the Bratton and Marshall procedure. Since there is a straight line relationship between the extent of hydrolysis of PABA-cholic and the quantity of bacteria present, this in vitro assay can be used to measure the presence of bacteria in this intestinal fluid by comparing the result obtained with an extablished standard.

This same in vitro test can be used to assay the concentration of bacteria in other preparations or systems such as biological fluids including milk, blood, feces, bile, pancreatic juice, urine, etc. These are short-time tests in contrast to the long time required to incubate a suspected biological fluid in a nutrient medium and microscopically examine it for bacteria.

We claim:

1. A method for detecting in the intestines of an animal organism an overgrowth of bacteria which are normally present there in lesser amounts, such an abnormal concentration manifesting itself by symptoms which are common to other physical maladies, which comprises orally administering to said animal a measured amount of a chemical conjugate one component of which is selected from the group consisting of:

cholic acid
chenodesoxycholic acid
lithocholic acid
dehydrocholic acid
cholanic acid
allocholanic acid
dehydrodesoxycholanic acid
desoxybilianic acid
isodesoxybilianic acid
bilianic acid
etiocholanic acid
12-ketocholanic acid
hyodesoxycholic acid
norcholanic acid
ursocholanic acid
hyobeoxycholic acid
5-$\beta$-cholanic acid-3$\alpha$,6$\alpha$-diolacetate
5-$\beta$-cholanic acid-3$\alpha$,12$\alpha$-diol difurmate
5-$\beta$-cholanic acid-7$\alpha$,12$\alpha$-diol
5-$\beta$-cholanic acid-3$\alpha$,7$\alpha$-diol-12-one
7-ketodeoxy cholic acid
7,12-diketocholanic acid
3,12-diketocholanic acid, and
3,7-diketocholanic acid and the other component of which is para-amino benzoic acid which is absorbed from the intestines and excreted in the urine without substantial metabolic alteration, said conjugate being one which is cleaved into said components by the enzymes produced by said intestinal bacteria, collecting urine from said animal at a time interval after such administration and assaying it for said amino acid content, a content higher than an established average content found in urine from like healthy animals under the same method conditions being taken as indicative of an overgrowth of intestinal bacteria.

2. The method of claim 1 in which cholic acid is one component of the conjugate

3. The method of claim 1 in which from 0.5 mg. to 2.0 gms. per Kg. of body weight of the animal is administered.

4. The method of claim 1 in which the urine is collected at periodic successive intervals for comparison purposes.

* * * * *